United States Patent [19]

Livesey et al.

[11] Patent Number: 5,622,867
[45] Date of Patent: Apr. 22, 1997

[54] PROLONGED PRESERVATION OF BLOOD PLATELETS

[75] Inventors: Stephen A. Livesey, Eltham, Australia; Jerome Connor; Laura M. Currie, both of Houston, Tex.

[73] Assignee: Lifecell Corporation, The Woodlands, Tex.

[21] Appl. No.: 326,036

[22] Filed: Oct. 19, 1994

[51] Int. Cl.$^6$ .................................................. A61K 35/14
[52] U.S. Cl. .............................. 436/18; 436/63; 436/176; 435/2; 424/532
[58] Field of Search ..................................... 436/8, 12–18, 436/63, 176; 435/2; 424/532

[56] References Cited

U.S. PATENT DOCUMENTS 4,940,581  7/1990  Mason et al. ........................... 424/532
5,256,559  10/1993  Maraganore et al. ............... 435/240.2

OTHER PUBLICATIONS

Becker et al. "Effect of PGE1 on harvesting of plates from . . . " J. Lab. Clin. Med. (1974), abs 80:93687 CA.
Teng et al. "Platelet aggregation induced by equinatoxin" Thromb. Res. (1988) 52 (5) 401–11.
Teng et al "Triwaglerin: a potent platelet aggregation . . . " Biochim. Biophys. Acta (1989), 992(3), 258–64.
Narayanan "Inhibition of in vitro platelet aggregation . . . " Ann. Clin. Lab. Sci. (1989) 19(4), 260.5.
Two entries of the same abstract of Stephen Lindsey's "*Confidential Proposal to Small Business Innovation Research (SBIR) Program*" found in the Federal Research in Progress Data Base on Dialog. We do not know the publication date of these abstracts.
R. Valeri, H. Feingold, and L.D. Marchionni, *A Simple Method for Freezing Human Platelets Using Dimethylsulfoxide and Storage at –80°C*, Blood, vol. 43, No. 1 (Jan.), 1974.
A.P. Bode, S. Holme, W.A. Heaton, and M.S. Swanson, *Extended Storage of Platelets in an Artificial Medium with the Platelet Activation Inhibitors Prostaglandin E, and Theophylline*, Vox Sang 1991;60;105–112.

*Primary Examiner*—James C. Housel
*Assistant Examiner*—Rachel Heather Freed
*Attorney, Agent, or Firm*—Arnold, White & Durkee

[57] ABSTRACT

This invention provides a method for prolonging the preservation of human blood platelets at reduced temperatures. The method uses an inhibitor system that enables blood platelets to maintain their discoid shape and retain their functional integrity during storage. This is accomplished by interrupting normal platelet function during storage, so as to help keep platelets from activating and losing their shape. Before using the platelets in a transfusion, they are returned to their normal functional level by washing the inhibitor system away from the platelets.

25 Claims, No Drawings

5,622,867

PROLONGED PRESERVATION OF BLOOD PLATELETS

BACKGROUND OF THE INVENTION

1. Field of the Invention

This invention relates to a method for extending the shelf-life of human blood platelets. The invention relates particularly to a reversible inhibitor system and method that inhibits platelets from biologically activating during storage at refrigeration temperatures (4° C.) or freezer temperatures (−80° C.), but leaves platelets with the ability to resume normal reactions once the inhibitor system is removed. The composition and method of this invention enables storage of platelets at cryo-temperatures with recovery of function at a level previously impossible to achieve.

2. Description of Related Art

Platelet transfusions are frequently used to treat patients. Not only are platelet transfusions given to casualty victims suffering from massive blood loss, but also to patients undergoing chemotherapy. Chemotherapy reduces the number of a patient's platelets, and also causes the platelets that are present to function defectively. For example, with thrombocytopenia, a patient has a decreased number of platelets caused by bone marrow suppression, whereas a patient with hemorrhagic myocarditis may have platelets that have been rendered functionally defective by chemotherapy. Platelet transfusions are used to increase the number of platelets to treat conditions such as thrombocytopenia, and to replace functionally defective platelets in treating hemorrhagic myocarditis.

Blood platelets should be stored at the lowest temperature possible to reduce metabolic function and contaminant growth. Currently, platelets are stored for up to 5 days at 22° C. This storage time is limited by a decrease in pH due to increased lactate associated with anaerobic metabolic activity. Storage at 22° C. is also limited by the potential for bacterial growth. Refrigeration offers advantages over 22° C. storage with respect to metabolic function, contamination, and pH stability. However refrigerated storage results in multiple inherent problems. First, platelets undergo a change from discoid shape to a spherical configuration after about 24 hours of refrigerated storage. Second, spontaneous aggregation is increased after 24–48 hours of refrigerated storage. Third, platelets stored at 4° C. fail to recover functional activity following the storage period. Finally, platelets which undergo a storage lesion at 4° C. are cleared from the circulation by the spleen following transfusion.

Goals for refrigerated platelet storage are to preserve a high number of platelets, lengthen the time that platelets may be preserved, maintain the functional integrity of platelets and ensure that their in vivo circulatory life span approaches normal limits. This may be accomplished by using the inhibitor system of this invention, because it blocks pathways that are essential to activation, thus rendering the platelet unsusceptible to 4° C. induced damage.

Since fresh platelets have a shelf-life of only 3 to 5 days at 22° C. (room temperature), methods for extending platelet shelf-life would be beneficial. Unfortunately, despite a number of attempts to optimize platelet storage, progressive changes in cell shape (resulting in biological disfunction) and permanent deterioration in subsequent aggregation potential continue to limit platelet storage. In addition, platelets develop a lesion with storage that causes them to be removed from the circulation, predominantly by the spleen during the first passage following transfusion. For instance, the typical life span of a normal platelet in the human body is approximately eight days. Prior art attempts to store platelets for extended periods of time result in the creation of lesion-modified platelets. Approximately 80%–90% of the prior art storage platelets can be numerically recovered after storage, but only 20%–35% remain active after the first circulatory flow through the spleen. This is because the spleen filters out the lesion-modified platelets. Use of the compositions and methods of this invention result in the same 80%–90% numerically recovered as the prior art, but since lesion-modified platelets are not produced, 65% to 80% of the reactivated platelets should function biologically for the typical time in the human body.

Several approaches such as reduced storage temperature, cryopreservation techniques, additives and artificial storage media yield an increased number of platelets following storage. However, the functional capacity and persistence in circulation of the platelets recovered by these methods is limited. Blood banks and hospitals very much need a platelet storage system that provides an increased number of platelets after storage, but also prevents platelets from aggregating during storage and enables them to continue to retain the ability to react normally once they are transfused into a patient including the ability of platelets to persist in the circulation and not be cleared.

Blood banks and hospitals very much need a platelet storage system that will provide an increased number of platelets after storage. This may be accomplished by a platelet storage system that: prevents platelets from aggregating during storage; enables platelets to regain the ability to react normally after removal from storage; and allows platelets to persist in circulation and avoid being cleared by the spleen.

Previous attempts to use platelet activation inhibitors have met with very limited success. This is primarily because the prior art teaching is limited to the use of a single inhibitor in an attempt to preserve platelet function. The single inhibitor system results in improved results over no inhibitor at all but does not approach the unexpected results achieved using the compositions and methods of the subject invention. Prior methods for the use of single inhibitor systems are explained in Valeri, Feingold, and Marchionni, *A Simple Method for Freezing Human Platelets Using Dimethylsulfoxide and Storage at −80° C.*, Blood, Vol. 43, No. 1 (January), 1974 and Bode, Holme, Heaton, and Swanson, *Extended Storage of Platelets in an Artificial Medium with the Platelet Activation Inhibitors Prostaglandin E, and Theophylline*, Vox Sang 1991; 60; 105–112.

The instant invention represents a quantum leap in beneficial result and technical sophistication over the prior methods. The platelet storage, reactivation, and long term functional effectiveness of blood platelets treated with the compositions and methods of this invention have previously been considered impossible.

SUMMARY OF THE INVENTION

This invention provides a method for prolonging the preservation of human blood platelets. The method uses an inhibitor system that enables blood platelets to maintain their discoid shape and retain their functional integrity during prolonged storage. This is accomplished by inhibiting normal platelet function, so as to help keep platelets from biologically activating during storage.

The method of this invention broadly comprises an inhibitor system that is made up of second messenger effectors.

This second messenger inhibitor system functions through the following pathways: cyclic adenosine monophosphate (cyclic AMP), sodium channel, cyclic guanosine monophosphate (cyclic GMP), cyclooxygenase, lipoxygenase, phospholipase, the calcium cascade, protease and proteinase, and membrane modification. More specifically, special agents or combinations of agents may be used for each of the pathways. For example, adenosine, iloprost, prostacyclin and $PGE_2$ act to inhibit activation through stimulation of the cyclic AMP pathway. Amiloride and amiloride analogues act to inhibit activation through inhibition of the sodium channel. Sodium nitroprusside and L-arginine act to inhibit activation through stimulation of the cyclic GMP pathway. Aspirin, dipyridamole, flurbiprofen, and ticlopidine act to inhibit activation through inhibition of the cyclooxygenase pathway. Aspirin and ticlopidine act to inhibit platelet activation through inhibition of the lipoxygenase pathway. Quinacrine acts to inhibit platelet activation through the inhibition of the phospholipase pathway. Calcium acts to promote platelet activation through the calcium cascade. Protease and or proteinases act to inhibit platelet aggregation through the inhibition of surface receptor changes. Amantadine, ajoene, heparin, ticlopidine, and/or pentoxifylline act as membrane modifiers.

The inhibitor systems described previously function during storage at low temperatures, i.e. from 2° to 8° C. When subzero storage temperatures (−20° to −135° C.) are used, it is beneficial to introduce a cryoprotective agent to the platelets before cryopreparation. Examples are dimethyl sulfoxide, maltodextrins, dextran, hydroxyethyl starch and glucose, although other cryoprotectants may also be used. Cryoprotectants may be used individually or in combination.

A preferred method for human platelet preservation begins by drawing whole human blood via venipuncture into an evacuated tube containing an anticoagulant. The blood is centrifuged to isolate platelet-rich plasma from the blood. The platelet-rich plasma is centrifuged to separate platelet-poor plasma from the platelet pellet, which is the concentrated platelets left after centrifuging and decanting the plasma. Next, an inhibitor system is added to the platelet-poor plasma. This inhibitor system is comprised of solutions of the following substances that are added to the platelet-poor plasma and result in the following concentrations: from 0.1 mM to 10 mM, preferably about 1 mM amiloride in dimethyl sulfoxide (DMSO); from about 2.5 uM to about 250 uM, preferably about 25 uM sodium nitroprusside (NaNP) in phosphate buffered saline; from about 10 uM to about 1 uM, preferably about 0.1 mM adenosine in phosphate buffered saline; from about 10 nM to about 1 uM, preferably about 0.1 uM quinacrine in phosphate buffered saline; from about 2 uM to about 200 uM, preferably 20 uM dipyridamole in DMSO; from about 0.5 mM to about 5 uM, preferably 1.5 mM ticlopidine in DMSO; and from about 5 units/ml to about 200 units/ml, preferably 20 units/ml heparin in phosphate buffered saline. The platelet pellet is gently resuspended in the platelet-poor plasma/inhibitor system mixture. The mixture is then placed in a platelet storage container and stored at (2°–8° C.) without agitation. An alternative method of adding the inhibitors is to cream a suspension of the inhibitors described but without the addition of DMSO. The suspension is then lyophilized. At the time of addition, the lyophilized powder of inhibitors is rehydrated with platelet poor plasma and then added to the platelet pellet. Other aspects of the process and concentration ranges of the inhibitors are as described above.

The same steps used for 4° storage are used for platelets stored at −20° to −135° C., with two exceptions. The cryoprotective agent, dimethyl sulfoxide, makes up a part of the inhibitor system used for −20° to −135° C. storage, and the platelet storage container must be one suitable for storage at −20° to −135° C.

DETAILED DESCRIPTION OF THE PREFERRED EMBODIMENTS

Activation during storage is undesirable. However, platelets must retain the ability to activate when they are taken out of storage to function normally for transfusion purposes. When the platelets are removed from storage, the inhibitor system of this invention may be washed from the platelets, which allows them to return very closely to their normal level of activity. This washing step can be achieved in vitro by mechanical washing or by a dilution effect from direct transfusion.

There are three platelet activity parameters that are measured to determine whether platelets have retained their functional ability after storage. These parameters are useful when they are compared to the same parameters for fresh platelets. Additionally, the platelet activity parameters for platelets stored with different inhibitor mixtures may be compared to determine which inhibitor combinations yield more functional platelets after storage. The tests used to measure platelet activity parameters preserved by this invention are: platelet number, hypotonic stress-response, collagen-induced aggregation and adenosine diphosphate (ADP)-induced aggregation. In addition, measurement of granule release yields important information about the integrity of the platelets during storage.

Hypotonic stress response is an assay used to determine if platelets have retained metabolic viability. This assay is a photometric measurement of the platelets' ability to overcome the addition of a hypotonic solution. This activity reflects cell function (i.e. a functional membrane water pump) and is indicative of platelet recovery following storage. Hypotonic stress response has been demonstrated to be an important indicator of platelets' ability to survive in circulation following transfusion. Consequently, hypotonic stress response represents a crucial parameter for evaluating platelet biochemistry following storage.

Potential for aggregation is another feature that demonstrates whether blood platelets have maintained their functional integrity during storage. This potential is measured by using ADP and collagen to induce aggregation. An agonist is an agent that binds to a receptor and initiates a certain response. In an agonist-induced aggregation, the aggregation or clumping is the response. The agonists, ADP and collagen, are used to induce aggregation to determine if platelets have retained their ability to aggregate. In addition, when performing aggregation responses one can detect the presence of spontaneous aggregation, that is the platelets adhering to each other without the addition of an agonist. The occurrence of spontaneous aggregation has been correlated with removal of platelets from the circulation and hence have short survival times.

A. THE INHIBITOR SYSTEM

The inhibitor system of this invention is based on the application of specific second messenger effectors, which interact with the platelets and stabilize the cells to resist loss of viability and functional activity during storage at 4° C. and at −80° C..

The Seven Component Mixture

Specific modifiers that make up the preferred seven component inhibitor system are amiloride, adenosine, sodium nitroprusside, quinacrine, dipyridamole, ticlopidine and heparin. These modifiers are added to the platelet pellet following dilution (from a 100-fold concentrate) into autologous platelet-poor plasma. Each of these modifiers affects a different specific second messenger pathway. Amiloride is a potassium conserving diuretic, employed medicinally in the treatment of hypertension. In this invention, amiloride acts as an inhibitor of the platelet $Na^+$-$H^+$ exchanger. Adenosine is used medicinally to restore normal sinus rhythm in patients. In this invention, adenosine stimulates the production of cyclic AMP. Sodium nitroprusside relaxes smooth muscle thus serving as a vasodilator, medicinally. In this invention, sodium nitroprusside stimulates the production of cyclic GMP. Dipyridamole is employed medicinally as a platelet adhesion inhibitor. In this invention, dipyridamole acts as an inhibitor of cyclooxygenase and lipoxygenase enzymes of the arachidonic acid cascade. Quinacrine is used in the treatment to eradicate intestinal cestodes. In this invention, quinacrine serves as a phospholipase $A_2$ inhibitor. Medicinally, ticlopidine is used as a platelet aggregation inhibitor to reduce the risk of thrombotic strokes. In this invention, ticlopidine is used as an inhibitor of the arachidonic acid cascade. Heparin is employed medicinally as an anti-clotting agent in blood. In this invention, heparin is used to block fibrin binding.

All of the second messenger effectors have been demonstrated to inhibit agonist induced aggregation both separately and in combination with the others. More importantly, the inhibition is reversible following removal of the effector(s) by washing the platelets. Upon adding the second messenger effectors, both individually or in combination, platelets were less susceptible to storage lesions during storage at 2° to 8° C. or at −20° to −135° C. These cells also displayed normal aggregation physiology upon removal of the effector(s), they also did not display spontaneous aggregation and maintained a high hypotonic stress response.

In describing the chemicals which have shown utility as platelet lesion inhibitors, it must be understood that the actual chemicals mentioned together with functionally equivalent materials are intended to be within the scope of this invention. Chemicals that are known to applicants to have known or demonstrated utility as inhibitors have been specifically set forth in the instant application. However, it is intended that the scope of the application be extended to other functionally effective chemicals, both existing chemicals and chemicals yet to be discovered.

Certain chemicals which are thought to be functionally equivalent materials for the effectors of the cyclic AMP second messenger system are those selected from the group consisting of adenosine, iloprost, prostacyclin, $PGE_2$, forskolin, cholera toxin, isoproterenol, 8-bromo cAMP, dibutyl cAMP, isobutylmethyl xanthine, thyrotropin, theophylline and auranofin. Materials thought to be functionally equivalent to the inhibitor acting through the sodium channel are those selected from the group consisting of amiloride, amiloride analogues, bepridil, flecainide, saxitoxin, benzamil and prajnalium. Materials thought to be functionally equivalent to the inhibitor acting through the GMP pathway are selected from the group consisting of sodium nitroprusside, L-arginine, nitrous oxide, SIN-1, SIN-1A, atrial natriuretic factor, vasopressin, oxytocin, and glyceryl trinitrate. Functionally equivalent materials for the inhibitor acting through the cyclooxygenase pathway are selected from the group consisting of aspirin, dipyridamole, flurbiprofen, and ticlopidine, ketoprofen, ibuprofen, indomethacin, sulfinpyrazone, guanabenz, ursolic acid and benzohydroquinone. Functionally equivalent materials for the inhibitor component acting through the lipoxygenase pathway are selected from the group consisting of aspirin, ticlopidine, ursolic acid, unbelliferone, 5,8,11,14 eicosatetraynoic acid and esculetin. Finally, functionally equivalent materials to the inhibitor acting through the calcium cascade are selected from the group consisting of protein kinase C effectors, calcium channel blockers, calcium concentration modifiers, calmodulin effectors, calcium ionophores and ATPase stimulators.

B. STORING PLATELETS AT 4° C.

The shelf-life of blood platelets may be successfully extended by storing the cells at 4° C. with the inhibitor system of this invention. When platelets that were stored at 4° C. for 10 days were analyzed for post-storage activity, as compared to the activity of fresh platelets, the percentage of the cells' activity was as follows: 70% ADP-induced aggregation, 85% collagen-induced aggregation, 65% hypotonic stress response and >95% recovery of cell number. These results compare favorably to conventional storage of platelets at 22° C. following 5 days of storage which yielded 55% ADP-induced aggregation, 80% collagen-induced aggregation and 50% hypotonic stress response, as compared to fresh platelets.

To perform the 4° C. experiment, whole blood is drawn via venipuncture into blood bags containing the anti-coagulant acid-citrate dextrose as prescribed by the procedures and protocols of the American Association of Blood Banks and performed by a blood procurement agency. To perform small scale experimentation, whole blood can also be drawn into 6 milliliter evacuated tubes and processed by the same protocols as with the blood bags. The blood bags are centrifuged at 2000×g for 3 minutes to separate the red blood cells from the platelets and the plasma. The platelet-rich plasma is isolated by expression into a connected platelet storage bag followed by a second centrifugation at 5000×g for 5 minutes to pellet the platelets. The platelet-poor plasma is expressed into a plasma storage bag, while the resulting platelet pellet, with approximately 50–60 milliliters of plasma is left for one hour at 22° C. as prescribed by blood banking procedures. Following the incubation, the platelet preparation is resuspended in the residual plasma by gentle shaking. In the small scale experiments in 6 milliliter tubes, an equivalent volume of plasma is left on the platelet pellet and the platelet sample is resuspended.

An inhibitor system solution is prepared as follows: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 uM quinacrine, and 2,000 units/ml of heparin. The concentration of the inhibitor system reagents in these mixtures is 100-fold the final concentration needed in the platelet preparation to achieve effective storage at 4° C. The inhibitor solutions are added to the platelet concentrate at a 1/100 volume of the total platelet preparation volume via a direct injection through a sterile port. The order of addition of the DMSO solution and the phosphate-buffered saline solution is not believed essential to the practice of the invention. The final concentration of the inhibitor reagents in the platelet preparation is as follow: amiloride—1 mM, adenosine—0.1 uM, sodium nitroprusside—25 uM, dipyridamole—20 uM, quinacrine—0.1 uM, ticlopidine—1.5 mM, and heparin 20 units/ml. The platelet preparation in a standard platelet storage bag is placed at 4° C. without agitation. The platelet concentration with the inhibitor system can be directly transfused following storage.

Alternatively the combination of inhibitors can be added to the platelet pellet in the absence of DMSO. This can be achieved in two ways. The combination of inhibitors can be processed to a suspension by sonication. This sonicated suspension can then be used directly as described above. Alternatively, the sonicated suspension can be lyophilized and stored as a lyophilized powder. Upon use, the powder is rehydrated with an appropriate volume of platelet poor plasma and added to the platelet pellet as described above. Using either method, the final concentration of additives (excepting the absence of DMSO) is the same as described above.

C. STORAGE OF PLATELETS AT −20° TO −135° C. BY CRYOPRESERVATION

A second use of this invention involves the storage of platelets at −20° to −135° C. The addition of the inhibitor solution system of this invention to the platelet pellet effectively stabilizes the platelets thus allowing the cells to be successfully cryopreserved and stored at −20° to −135° C.

Storing platelets at −20° to −135° C. requires the addition of a cryoprotective agent. As part of the process of this invention dimethyl sulfoxide (DMSO) serves as the cryoprotectant. DMSO is a polar molecule which penetrates the cell membrane and serves to preserve cell viability during the cryopreparation process. DMSO functions in this invention to stabilize the platelets allowing recovery of functionally active platelets after storage at −20° to −135° C. After long term storage of platelets (>100 days) that were cryopreserved with the inhibitor system of this invention, the number of cells recovered and the functional activity of the platelets was compared to that of fresh platelets. More than 95% of the cryopreserved cells were recovered and these platelets displayed a functional activity of 55% ADP-induced aggregation, 65% collagen aggregation and 50% hypotonic stress response. These results compare favorably to conventionally stored platelets following 5 day storage at 22° C. In addition, other cryoprotectants may be substituted for the DMSO in this protocol; these include maltodextrin, dextran, hydroxylethyl starch, and glucose, either individually or in combination.

To process platelets for the use of the inhibitor storage system of this invention, a platelet concentrate is generated as prescribed by blood banking procedures and detailed in the 4° C. storage section (B). An inhibitor system solution is prepared as followed: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 uM quinacrine, and 2,000 units/ml of heparin. The concentration of the inhibitor system reagents in these mixtures is 100-fold the final concentration needed in the platelet preparation. The inhibitor solutions are added to the platelet concentrate at a 1/100 volume of the total platelet preparation volume via a direct injection through a sterile port. The order of addition of the DMSO solution and the phosphate-buffered saline solution is irrelevant. The final concentration of the inhibitor reagents in the platelet preparation is as follows: amiloride—1 uM, adenosine—0.1 mM, sodium nitroprusside—25 uM, dipyridamole—20 uM, quinacrine—0.1 uM, ticlopidine—1.5 mM, and heparin 20 units/ml. In addition, DMSO is added directly to the platelet preparation via injection through a sterile port to a final concentration of between 1% and 6%, preferably 2%. The platelet storage bag, compatible with storage at −20° to −135° C., is placed in a standard freezing cassette followed by placement in a −20° to 135° C. freezer. Following storage of the platelets at −20 to 135° C. with the inhibitor system of this invention, the platelet preparation is removed from the −20° to −135° C. freezer and directly placed in a 37° C. water bath until the entire preparation is thawed. The platelet concentrate with the inhibitor system can be directly transfused following the thawing procedure. Alternatively, the platelet preparation can be centrifuged to pellet the platelets, thus removing the DMSO component of the cryopreservation solution. These platelets can then be resuspended in autologous plasma and directly transfused.

The following examples are provided to enable those of ordinary skill in the art to make the compositions of this invention. These examples are not intended to limit the scope of what the inventors regard as their invention. Efforts have been made to ensure accuracy with respect to numbers used to characterize the measured conditions; however, some experimental errors and deviations may be present.

EXAMPLE 1

The following example describes results of experiments testing prolonged storage at 4° C. Six tubes of whole blood were drawn via venipuncture of the antecubital vein into 6 milliliter draw evacuated tubes containing acid-citrate dextrose anticoagulant. The tubes containing whole blood were centrifuged at 250×g for 12 minutes. Platelet-rich plasma was isolated. The platelet-rich plasma was centrifuged at 950×g for 20 minutes. All the platelet-poor plasma was removed from the pellet. Solutions were added to the platelet-poor plasma that resulted in the following final concentrations: 1 mM amiloride; 25 uM sodium nitroprusside (NaNP); 0.1 mM adenosine in phosphate buffered saline; 0.1 uM quinacrine; 20 uM dipyridamole; 1.5 mM ticlopidine; 20 units/ml heparin and 1% DMSO. The platelet-poor plasma containing the solutions was returned to the platelet pellet to a volume of 1/10 of the original platelet-rich volume. The pellet was gently resuspended and the mixture was transferred to a platelet storage bag. The platelet bag with the mixture was stored at 4° C. without agitation.

Results of the Above Method After 10 Day Storage at 4° C.

Following ten (10) days storage at 4° C. in standard platelet storage bags, the platelets were warmed to room temperature and diluted with autologous plasma to the original platelet-rich plasma volume. The platelets were analyzed for post-storage activity as compared to the activity of fresh platelets. The results of the activity profile are as follows:

ADP-Induced Aggregation—70%

Collagen-Induced Aggregation—85%

Hypotonic Stress Response—65%

Platelet Cell Number Recovery—95%

EXAMPLE 2

The following example describes an experiment to measure platelet activity after storage at −80° C. Six tubes of whole blood were drawn via venipuncture of the antecubital vein into 6 milliliter draw evacuated tubes containing acid-citrate dextrose anticoagulant. The tubes containing whole blood were centrifuged at 250×g for 12 minutes. Platelet-rich plasma was isolated. The platelet-rich plasma was centrifuged at 950×g for 20 minutes. All the platelet-poor plasma was removed from the pellet. Solutions were added to the platelet-poor plasma that resulted in the following final concentrations: 1 mM amiloride; 25 uM sodium nitroprusside (NaNP); 0.1 mM adenosine; 0.1 uM quinacrine; 20 uM dipyridamole, 1.5 mM ticlopidine; 20 units/ml heparin and 6% dimethyl sulfoxide. The platelet-poor plasma containing the solutions was returned to the platelet pellet to a volume of 1/10 the original platelet-rich volume. The pellet was gently resuspended and the mixture was transferred to a platelet storage bag. The platelet bag with the mixture was stored at −80° C. in a standard red blood cell cassette designed for freezing.

Results of the Above Method After Cryopreservation

Following a thaw, by directly placing the frozen platelet sample into a 37° C. water bath, the platelets were diluted with autologous plasma to the original platelet-rich plasma volume. The platelets were analyzed for the post storage activity profiles as compared to fresh platelets and the results are as follows:

ADP-Induced Aggregation—50%

Collagen-Induced Aggregation—74%

Hypotonic Stress Response—78%

Platelet Cell Number Recovery—85%

EXAMPLE 3

The following describes an example of the application of the inhibitor system of this invention to the storage of a whole unit platelet concentrate for extended period at 4° C. A whole unit of whole blood was drawn via venipuncture at the Gulf Coast Regional Blood Bank according to standard blood banking techniques into a sterile commercial blood collection system. The blood bag containing the whole blood was centrifuged according to standard blood banking procedures and the resultant platelet-rich plasma fraction was expressed into a standard platelet storage bag. The platelet-rich plasma was then centrifuged according to the blood banking protocol and the resultant platelet-poor plasma was expressed into a standard plasma storage bag. The resultant platelet pellet in the platelet storage bag still retains approximately 60 milliliters of plasma. This platelet concentrate is stored without agitation for one hour at 22° C. to allow the platelets to resuspend. A solution of inhibitors is prepared which contains the following: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 uM quinacrine, and 2,000 units/ml of heparin. The concentration of the inhibitor system reagents in these mixtures is 100 fold the final concentration needed in the platelet preparation. The inhibitor solutions are added to the platelet concentrate at a 1/100 volume of the total platelet preparation volume (approximately 0.6 milliliters) via a direct injection through a sterile port. The order of addition of the DMSO solution and the phosphate-buffered saline solution to the platelet concentrate is irrelevant. The final concentration of the inhibitor reagents in the platelet preparation is as follows: amiloride—1 uM, adenosine—0.1 uM, sodium nitroprusside—25 uM, dipyridamole 20 uM, quinacrine—0.1 uM, ticlopidine—1.5 mM, and heparin 20 units/ml. The platelet concentrate with the inhibitor solution is then stored at 4° C., without agitation. In parallel, as a means of comparison, a platelet concentrate unit was stored under the current blood banking method as follows: after the one hour incubation of the platelet concentrate to allow resuspension, the platelet preparation was stored at 22° C. with gentle agitation following standard blood banking procedures. In addition, a platelet concentrate preparation was stored at 4° C. without the inclusion of the inhibitor system. At various time intervals of storage, an aliquot of platelets was harvested from the conventionally stored preparation, the platelets stored at 4° C., and the platelets stored at 4° C. with the inclusion of the inhibitor solution of this invention. Platelets from these preparations were then analyzed for viability and functional activity of the cells. The results of this experiment are shown in the following table. The data is expressed as a percentage of the viability and functional activity of fresh platelets at the time of acquisition.

| | % of Fresh Platelets | | | | | |
|---|---|---|---|---|---|---|
| | ADP-Induced Aggregation | | Collagen-Induced Aggregation | | Hypotonic Stress Response | |
| Time (days) | 5 | 10 | 5 | 10 | 5 | 10 |
| 22° C. Storage | 32 | 28 | 67 | 42 | 35 | 57 |
| 4° C. Storage | 23 | 15 | 44 | 31 | 34 | 22 |
| Inhibitor System Storage | 54 | 58 | 89 | 83 | 86 | 65 |

In all tests of viability and functional activity, the platelet concentrate stored at 4° C. with the addition of the inhibitor system of this invention displayed higher recovery at day 10 than the conventionally stored platelets at day 5. Under current blood bank practices the maximum storage time for platelets is 5 days at 22° C.

EXAMPLE 4

The following describes an example of the application of the inhibitor system of this invention to the storage of a whole unit platelet concentrate for extended period at −80° C. via cryopreservation. A whole unit of whole blood was drawn via venipuncture at the Gulf Coast Regional Blood Bank according to standard blood banking techniques into a sterile commercial blood collection system. The blood bag containing the whole blood was centrifuged according to standard blood banking procedures and the resultant platelet-rich plasma fraction was expressed into a standard platelet storage bag. The platelet-rich plasma was then centrifuged according to the blood banking protocol and the resultant platelet-poor plasma was expressed into a standard plasma storage bag. The resultant platelet pellet in the platelet storage bag still retains approximately 60 milliliters of plasma. This platelet concentrate is stored without agitation for one hour at 22° C. to allow the platelets to resuspend. A solution of inhibitors is prepared which contains the following: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 uM quinacrine, and 2,000 units/ml of heparin. The concentration of the inhibitor system reagents in these mixtures is 100 fold the final concentration needed in the platelet preparation. The inhibitor solutions are added to the platelet concentrate at a 1/100 volume of the total platelet preparation volume (approximately 0.6 milliliters) via a direct injection through a sterile-port. The order of addition of the DMSO solution and the phosphate-buffered saline solution to the platelet concentrate is irrelevant. The final concentration of the inhibitor reagents in the platelet preparation is as follows: amiloride—1 mM, adenosine—0.1 mM, sodium nitroprusside—25 uM, dipyridamole—20 uM, quinacrine—0.1 uM, ticlopidine—1.5 mM, and heparin 20 units/ml. In addition, DMSO is added to the platelet concentrate via injection through a sterile port to a final concentration of 6%. The platelet preparation in a standard freezer bag was put into a freezer cassette and placed at −80° C. In parallel, a platelet concentrate was cryopreserved according to the conventional blood banking methods, that is, the addition of 6% DMSO to the platelet concentrate followed by the placement of the platelet preparation at −80° C. in a freezer cassette. Following storage at −80° C. for 20 days, the platelet preparation was removed from the −80° C. freezer and placed directly into a 37° C. water bath. An aliquot of platelets was harvested and centrifuged to remove the DMSO. The platelet pellet was resuspended in autologous plasma and the viability and functional activity of the cells was determined. The results of this experiment are shown in the following table. The data is expressed as a percentage of the viability and functional activity of fresh platelets at the time of acquisition.

| Cryopreservation Conditions | % of Fresh Platelets | | |
|---|---|---|---|
| | ADP-Induced Aggregation | Collagen-Induced Aggregation | Hypotonic Stress Response |
| Conventional System | 0 | 13 | 7 |
| Inhibitor System | 58 | 76 | 61 |

The platelets stored via cryopreservation at −80° C., by employing the inhibitor system of this invention, display good recovery of viability and functional activity and thus are rendered capable to be effective following transfusion.

What is claimed is:

1. An inhibitor system effective to prolong the in vitro presentation of human platelets at temperatures of 8° C. and below, said system capable of inhibiting platelet activity during storage, but enabling platelet activity to resume after the inhibitor system is removed from the platelets, comprising: a plasma phase containing amiloride, sodium nitroprusside, adenosine, dipyridamole, quinacrine, ticlopidine and heparin in amounts effective to prolong storage time of bioactive platelets, said inhibitor system being functionally effective to block the cyclic AMP pathway, the sodium channel, the cyclic GMP pathway, the cyclooxygenase pathway, the lipooxygenase pathway, the phospholipase pathway, and the membrane modification pathway.

2. A platelet storage composition effective to prolong the in vitro preservation of platelets at temperatures of 8° C. and below comprising a plasma excipient for platelet storage which includes between about 0.1 mM and 10 mM amiloride, between about 2.5 uM and 250 uM sodium nitroprusside, between about 10 uM and 1 mM adenosine, between about 10 nM and 1 uM quinacrine, between about 2 uM and 200 uM dipyridamole; between about 0.5 mM and 5 mM ticlopidine, and between about 5 units/ml to about 200 units/ml heparin, said plasma excipient being functionally effective to block the cyclic AMP pathway, the sodium channel, the cyclic GMP pathway, the cyclooxygenase pathway, the lipooxygenase pathway, the phospholipase pathway, and the membrane modification pathway.

3. The composition of claim 2 further comprising between about 0.5% to about 10% of a cryopreservation agent.

4. The composition of claim 3 wherein said cryopreservation agent is between about 0.5% and 6% dimethyl sulfoxide.

5. The composition of claim 3 wherein said cryopreservation agent is dimethyl sulfoxide present at a concentration of about 2%.

6. The composition of claim 1 wherein said amiloride concentration is about 1 mM amiloride.

7. The composition of claim 1 wherein said sodium nitroprusside concentration is about 25 uM.

8. The composition of claim 1 wherein said adenosine concentration is about 0.1 mM.

9. The composition of claim 1 wherein said quinacrine concentration is about 0.1 uM.

10. The composition of claim 1 wherein said dipyridamole concentration is about 20 uM.

11. The composition of claim 1 wherein said ticlopidine concentration is about 1.5 mM.

12. The composition of claim 1 wherein said heparin concentration is about 20 units/ml.

13. A method for the prolonged in vitro storage of platelets at temperatures of 8° C. and below comprising the steps of:

adding an inhibitor system capable of inhibiting platelet activity during storage, but enabling platelet activity to resume after the inhibitor system is removed from the platelets, comprising a plasma phase containing amiloride, sodium nitroprusside, adenosine, quinacrine, dipyridamole, ticlopidine, and heparin, said inhibitor system being functionally effective to block the cyclic AMP pathway, the sodium channel, the cyclic GMP pathway, the cyclooxygenase pathway, the lipooxygenase pathway, the phospholipase pathway, and the membrane modification pathway;

mixing said inhibitor system with a preparation of platelets; and refrigerating.

14. The method of claim 13 wherein said plasma inhibitor mixture further comprises between about 0.5% to about 10% of a cryopreservation agent.

15. The method of claim 14 wherein said cryopreservation agent is between about 0.5% and 6% dimethyl sulfoxide.

16. The method of claim 14 wherein said cryopreservation agent is dimethyl sulfoxide present at a concentration of about 6%.

17. The method of claim 13 wherein said amiloride is added in a concentration of from about 1 uM.

18. The method of claim 13 wherein said sodium nitroprusside is added in a concentration of 25 uM.

19. The method of claim 1 wherein said adenosine is added in a concentration of about 0.1 uM.

20. The method of claim 13 wherein said quinacrine is added in a concentration of about 0.1 uM.

21. The method of claim 13 wherein said dipyridamole is added in a concentration of about 20 uM.

22. The method of claim 13 wherein said ticlopidine is added in a concentration of about 1.5 mM.

23. The method of claim 13 wherein said heparin is added in a concentration of about 20 units/ml.

24. A method for processing human blood comprising the steps of:

a. drawing whole blood from a person via venipuncture;

b. centrifuging the drawn blood to isolate platelet-rich plasma from the blood;

c. centrifuging the platelet-rich plasma to form a platelet-poor plasma and a platelet pellet;

d. adding to the platelet-poor plasma an inhibitor system comprising:
amiloride;
sodium nitroprusside;
adenosine;
quinacrine;
dipyridamole;
ticlopidine;
heparin;
said inhibitor system being functionally effective to block the cyclic AMP pathway, the sodium channel, the cyclic GMP pathway, the cyclooxygenase pathway, the lipooxygenase pathway, the phospholipase pathway, and the membrane modification pathway;

e. gently resuspending the platelet pellet in the platelet-poor plasma containing the inhibitor system; and f. storing resulting plasma containing the suspended pellet at a temperature of about 4° C.

25. A method for processing human blood comprising the steps of:

a. drawing whole blood from a person via venipuncture;

b. centrifuging the drawn blood to isolate platelet-rich plasma from the blood;

c. centrifuging the platelet-rich plasma to form a platelet-poor plasma and a platelet pellet;

d. adding to the platelet-poor plasma an inhibitor system comprising:
amiloride;
sodium nitroprusside;
adenosine;
quinacrine;
dipyridamole;
ticlopidine;
heparin;
dimethyl sulfoxide
said inhibitor system being functionally effective to block the cyclic AMP pathway, the sodium channel, the cyclic GMP pathway, the cyclooxygenase pathway, the lipooxygenase pathway, the phospholipase pathway, and the membrane modification pathway;

e. gently resuspending the platelet pellet in the platelet-poor plasma containing the inhibitor system and a cryoprotector; and f. storing resulting plasma containing the suspended pellet at a temperature of about −80° C.

* * * * *

UNITED STATES PATENT AND TRADEMARK OFFICE
CERTIFICATE OF CORRECTION

PATENT NO. : 5,622,867

DATED : April 22, 1997

INVENTOR(S) : Stephen A. Livesey et al.

It is certified that error appears in the above-identified patent and that said Letters Patent is hereby corrected as shown below:

Column 12, line 55, delete "1" and insert therefor --13--;

Column 12, line 56, delete "uM" and insert therefor -- mM.

Signed and Sealed this

Twenty-second Day of July, 1997

Attest:

BRUCE LEHMAN

Attesting Officer

Commissioner of Patents and Trademarks